US012775017B2

(12) United States Patent
Lührs

(10) Patent No.: US 12,775,017 B2
(45) Date of Patent: Oct. 27, 2026

(54) REACTION VESSEL

(71) Applicant: ALOIS DATA GMBH, Hannover (DE)

(72) Inventor: Thorsten Lührs, Braunschweig (DE)

(73) Assignee: ALOIS DATA GMBH, Hannover (DE)

( * ) Notice: Subject to any disclaimer, the term of this patent is extended or adjusted under 35 U.S.C. 154(b) by 466 days.

(21) Appl. No.: 18/575,955

(22) PCT Filed: Jul. 3, 2022

(86) PCT No.: PCT/EP2022/068360
§ 371 (c)(1),
(2) Date: Jan. 2, 2024

(87) PCT Pub. No.: WO2023/280731
PCT Pub. Date: Jan. 12, 2023

(65) Prior Publication Data
US 2024/0329059 A1 Oct. 3, 2024

(30) Foreign Application Priority Data
Jul. 5, 2021 (EP) .................................... 21183830

(51) Int. Cl.
*G01N 1/00* (2006.01)
*B01L 3/00* (2006.01)
*G01N 33/53* (2006.01)
*G01N 33/68* (2006.01)

(52) U.S. Cl.
CPC .... *G01N 33/6896* (2013.01); *B01L 3/502715* (2013.01); *G01N 33/5304* (2013.01); *B01L 2200/16* (2013.01); *B01L 2300/0654* (2013.01); *B01L 2300/168* (2013.01); *B01L 2400/0487* (2013.01); *G01N 2800/2828* (2013.01)

(58) Field of Classification Search
None
See application file for complete search history.

(56) References Cited

U.S. PATENT DOCUMENTS

2010/0071442 A1* 3/2010 Moon, Jr. .............. G01N 11/14
73/54.28

FOREIGN PATENT DOCUMENTS

| | | | |
|---|---|---|---|
| CN | 109265543 | A | 1/2019 |
| JP | H03-079834 | U | 8/1991 |
| JP | 2008513207 | A | 5/2008 |
| WO | 2012/110570 | A1 | 8/2012 |
| WO | 2016/001334 | A1 | 1/2016 |

* cited by examiner

*Primary Examiner* — Jyoti Mutreja
(74) *Attorney, Agent, or Firm* — WCF IP

(57) ABSTRACT

The invention provides a vessel for use in the analysis of samples comprising a housing, a lid closing the first end section of the housing, a stator arranged inside the housing for receiving a rotor, the rotor and the stator being spaced by a ring-shaped gap of constant radius, a shaft having a first end to which a magnetic shaft drive is fixed and an opposite second end covered by the rotor, wherein the shaft is run in a first bearing that is arranged on the shaft in an axial section arranged between the magnetic shaft drive and the rotor, and which first bearing is fixed to a lid.

16 Claims, 3 Drawing Sheets

REACTION VESSEL

Figure 1:
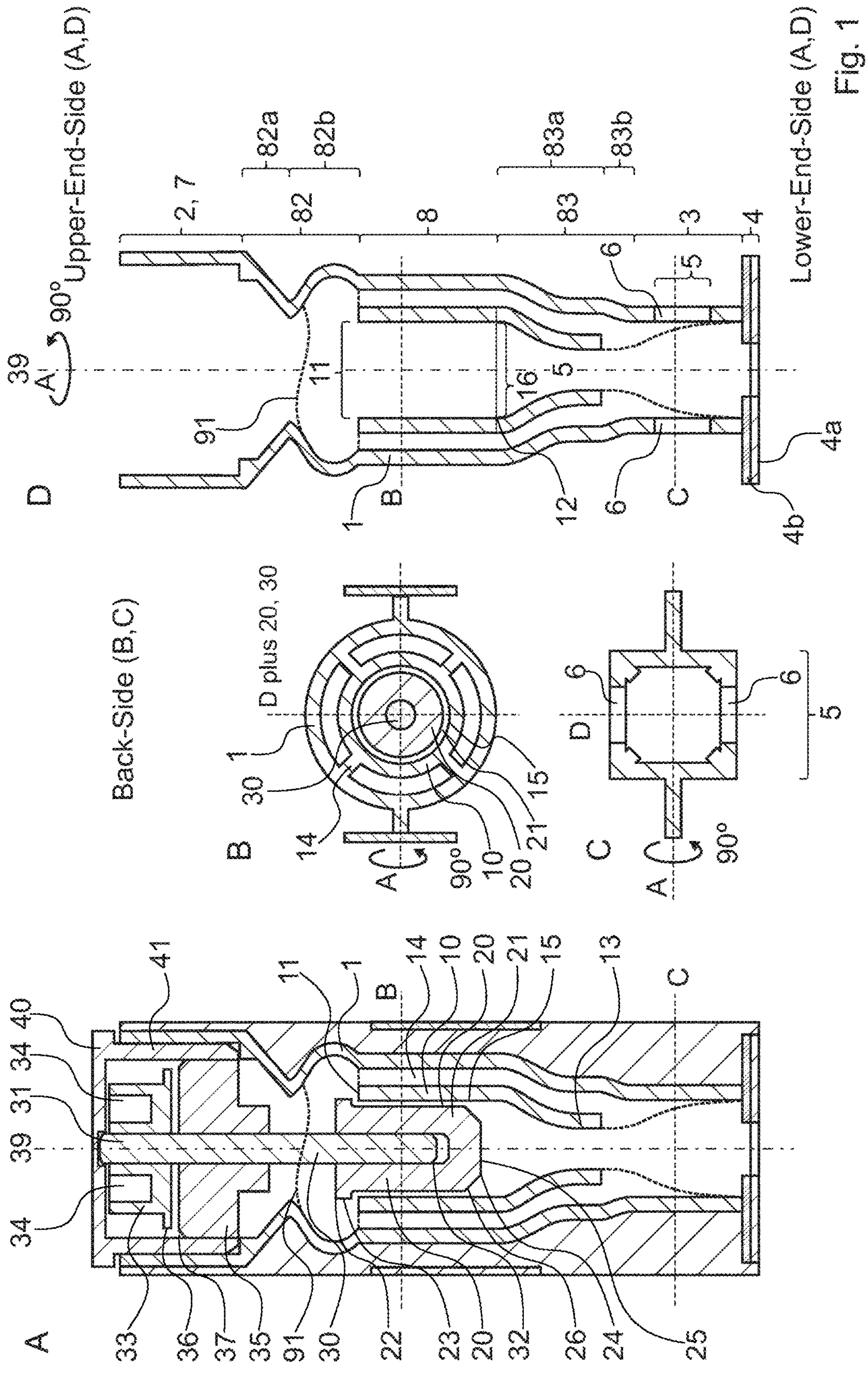

The present invention relates to a device that is a reaction vessel suitable for exerting defined shear force onto a liquid sample, a method for producing the reaction vessel, and to a process for exerting a defined shear force onto a sample, preferably including optical analysis of the sample through a portion of the reaction vessel.

The reaction vessel contains a rotor run on a bearing, preferably on exactly one bearing, the rotor having an axle which at one end has a driving section, suitable for receiving rotational torque from a drive motor that can be arranged adjacent to or at a distance from the driving section. Preferentially the bearing is arranged at a distance from a level of the liquid sample to be arranged in the vessel such that the bearing is not in contact with the liquid.

The reaction vessel contains a stator arranged co-axially with the rotor yielding a defined gap between rotor and stator, allowing the application of a defined shear stress to the liquid. The shear stress is proportional to the rotation frequency of the rotor, the radius of the rotor, and the viscosity of the liquid, and the shear stress is inversely proportional to the gap width between rotor and stator.

The reaction vessel allows for the circulation of the liquid sample when driven by the rotation of the rotor. The geometry of the vessel is designed in a way that the maximum shear stress is applied to the liquid in the section with the minimal gap width between rotor and stator.

The reaction vessel comprises a detection section, preferably arranged at its bottom end, which is at least in part optically transmissible, e.g. for light irradiating the inner volume of the reaction vessel and for detecting radiation passing through and/or radiation emitted from the inner volume of the reaction vessel.

STATE OF THE ART

WO 2012/110570 A1 schematically shows a reaction vessel in which a rotor is run on an axle that is run on a bearing located at the lid covering the vessel and a second bearing located at the bottom of the lid, with the rotor having a conical form that is parallel to the conically tapering bottom section of the vessel. In the alternative, the vessel is run on one sleeve arranged in the upper half of a cylindrical vessel, with the rotor extending into a tube section, open at both ends, which tube section is spaced from the rotor and is arranged in the lower half of the vessel with a spacing from the vessel bottom.

WO 2016/001334 A1 shows a reaction vessel within which a stator is inserted with a spacing from the vessel wall and spacing from the central rotor. The rotor is cylindrical with chamfered circumferential edges. The stator has extensions below its portion enclosing the rotor, and a light source and a detector are directed at 90° to one another and at 45° to the common central axis, and are directed into the space formed by the extensions.

OBJECT OF THE INVENTION

An object of the invention is to provide an alternative reaction vessel that is suitable for exerting shear stress onto a liquid, and an alternative process for exerting shear force onto a liquid by using the reaction vessel. A preferred object is to provide a reaction vessel that is set up for effectively exerting shear force on the entire volume of liquid contained in the vessel, and to provide a vessel that allows optical detection of a representative portion of the liquid.

DESCRIPTION OF THE INVENTION

The invention achieves the object by the features of the claims, and specifically by providing a reaction vessel that is suitable for subjecting the entire volume of a liquid contained in the vessel to shear force, while the vessel is set up for circulating the liquid through the vessel, the vessel comprising

- a housing having a first end section for connecting to a lid and an opposite second end section closed by a bottom wall, the second end section comprising a detection section which in the housing wall has at least one window section, preferably two window sections, wherein window sections are optically transparent and preferably plan, wherein the detection section preferably is arranged adjacent to the bottom wall,
- a lid, closing the first end section of the housing, the lid preferably having a recess arranged coaxially to the housing, wherein the lid preferably has cylindrical side walls clamping to a cylindrical section of the first end section of the housing,
- a stator, arranged inside the housing, which stator has a cylindrical inner surface for receiving a rotor with a constant spacing, the cylindrical surface having an open first end cross-section and an opposite second end cross-section, wherein the outer surface of the stator is arranged with a spacing from the housing, with at least three, preferably four, webs connecting the stator to the housing with a spacing, the webs preferably extending along a stator holding section of the housing only,
- wherein optionally the stator has its second end cross-sectional opening directly adjacent to the detection section or with a spacing from the detection section,
- wherein preferably an extension pipe is connected to the second end cross-section of the stator, the extension pipe having a constant cross-section or a cross-section tapering towards the detection section, the extension pipe terminating directly adjacent to the detection section or with a spacing from the detection section, which spacing can extend along a second section of a nozzle holding section,
- a rotor having or consisting of a cylindrical section arranged within the stator, the rotor and the stator being spaced by a ring-shaped gap of constant radius, the rotor having a second end that covers the second end of the shaft and which has a flat front face and a bevelled or rounded circumferential edge or which has a rounded front face, the rotor having at its first end terminal circumferential collar extending over the radius of the cylindrical rotor section and extending over cylindrical surface of the stator, the collar accordingly extending over the ring-shaped gap formed between the rotor and the stator,
- a shaft having a first end to which a magnetic shaft drive is fixed and an opposite second end covered by the rotor, wherein the shaft is run in a first bearing that is arranged on the shaft in an axial section arranged between the magnetic shaft drive and the rotor, and which first bearing is fixed to a lid, wherein preferably the first end of the shaft is a free end and is arranged in a recess of a lid, the shaft free end and the recess of a lid forming a second bearing, which is a frictional bearing, wherein the shaft, the magnetic shaft drive, the first bearing and the second bearing on which the shaft is run, the rotor, the stator, preferably the extension of the stator and/or the detection section, are arranged coaxially.

The ring-shaped gap of constant radius between the cylindrical rotor section and the cylindrical stator section forms an annular gap with constant cross-section.

Generally, the rotor, the circumferential collar of the rotor, the stator, the optional extension pipe, and the first bearing and the optional second bearing as well as the magnetic shaft drive are coaxial to the shaft, preferably all of the constituents of the vessel are coaxial to a common longitudinal axis, which is e.g. the longitudinal axis of the shaft.

In a detection section having two window sections, the window sections preferably are arranged at 90°, more preferably arranged parallel to one another in opposite sides of the housing wall.

Generally, the stator is arranged with a spacing from the housing, the spacing of the stator from the housing forming a channel for liquid to flow in the spacing from one end section of the stator, e.g. from its first end cross-section, to the opposite end section of the stator, e.g. to its second end cross-section, or to the opening of the extension pipe opposite to the stator. Accordingly, also the extension pipe is arranged with a spacing from the housing. As there is no relative movement between the stator and the housing in the spacing that forms the channel for liquid, there is significantly lower shear force in this channel, e.g. essentially no shear force in comparison to the shear force generated between the rotor and the stator, so that in the channel between the stator and the housing liquid can return to the gap between rotor and stator without being exposed to any relevant shear force. Preferably, the spacing of the stator from the housing is at least as large as the radius of the ring-shaped gap between the rotor and the stator in order to generate the maximum shear force between rotor and stator and to avoid significant shear forces when liquid flows through the spacing between stator and housing. The extension pipe is arranged coaxially to a nozzle holding section of the housing, wherein preferably the extension pipe is arranged with a constant spacing from the nozzle holding section of the housing.

Preferably, the cross-sectional area of the extension pipe is at least as large as the cross-sectional area of the ring-shaped gap between the rotor and the stator. Preferably, the extension pipe at each of its cross-sections or levels is circular.

The webs connecting the stator to the housing with a spacing can be formed with one of the stator and the housing with clamping connection between the webs and the respective other one of stator and housing, or the webs can be formed with both of the stator and the housing in one piece, e.g. by additive manufacturing, e.g. using a 3D-printer, for example using the fused deposition molding (FDM) technique. The embodiment, in which the stator, optionally the extension pipe connected to the second end of the stator, and the housing including the connecting webs are formed in one piece has the advantage of less strain and warp on the stator, e.g. compared to a stator clamped by webs into the housing.

Preferably, the rotor is spaced from the first bearing so that for the spacing the shaft is not covered. The spacing of the first bearing from the rotor provides for less contamination of the first bearing by liquid contacting the rotor.

Preferably, the housing in its section between the level of the lid or of the first bearing, e.g. the level of first bearing arranged in the lid, and the level of the rotor, has a diameter which is smaller than the outer or the inner diameter of the stator, and/or smaller than the diameter of the rotor, especially smaller than the diameter of the circumferential collar of the rotor. Such a section of smaller diameter is also interchangeably referred to as a collar section of the housing. Preferably, in the collar section, especially covering the section of the housing between the lid or the first bearing, e.g. the first bearing arranged in the lid, and the rotor, the shaft is not covered by the first bearing nor by the rotor. In a process using the vessel, preferably liquid is introduced into the housing up to at maximum the smallest cross-section of the collar section, and preferably up to a level completely filling the annular gap between the rotor and the stator.

The housing at its first end section preferably has a recess, preferably of cylindrical cross-section, for receiving a lid, e.g. for receiving cylindrical side walls of the lid, preferably with frictional fit, optionally including meshing of grooves and ridges of the outside of cylindrical side walls of the lid with grooves and ridges of the inside surface of the recess of the housing first end section.

Optionally, the housing in its section at the level of the circumferential collar of the rotor has an enlarged inner cross-section, e.g. broadens, compared to its section that is at the level of the second end of the stator and/or compared to the cross-section of housing section between the level of the lid or the level of first bearing, e.g. the first bearing arranged in the lid, and the level of the rotor. An enlarged inner cross-section of the housing at the level of the circumferential collar of the rotor has the advantage of guiding the liquid flow that is moved radially outwards by the rotating rotor, especially by its rotating circumferential collar, into the spacing between the stator and the housing, e.g. for generating a return flow of liquid to the second end cross-section of the stator, or to the cross-sectional opening of an extension pipe arranged opposite to the rotor and/or opposite to the stator.

The shaft preferably is a cylindrical stainless steel rod. Alternatively, the shaft can be a cylindrical rod of high-performance plastic.

Preferably, the first bearing is fixed, e.g. clamped, to the lid, e.g. the first bearing is clamped inside a recess formed by cylindrical side walls of the lid. The first bearing can be a bore in a plate, the bore providing a friction bearing for the shaft, optionally with radial guidance only and/or without axial guidance. The magnetic shaft drive preferably comprises or consists of a holder containing magnets, which holder is fixed, e.g. by clamping, to the shaft. The holder preferably has recesses for holding magnets, preferably recesses for holding one or two pairs of magnets. Along the shaft, the magnetic shaft drive is preferably arranged between the lid, the lid forming a second bearing for the first end of the shaft, and the first bearing which is fixed to the lid, e.g. by clamping in a recess formed by side walls of the lid, so that the magnetic shaft drive holds the shaft between the first bearing and the second bearing also when the first bearing is a bore that allows the shaft to axially slide. For restraining the axial movement of the shaft in the first bearing, the magnetic shaft drive can be fixed to the shaft in a position, in which the magnetic shaft drive is arranged adjacent to the first bearing, e.g. that the magnetic shaft drive contacts the first bearing, and in which position the first end of the shaft runs in the second bearing with the front face of the shaft contacting the recess of the lid with sufficient gap for allowing the shaft to rotate. Preferably, the magnets are neodymium magnets, e.g. cylindrical magnets arranged in borings of the holder. Alternatively other high performance magnets can be used, including hig performance composite magnets fabricated by injection molding Preferably, the shaft is a cylindrical metal rod, the magnets of the magnetic shaft drive are neodymium magnets, and all of the other constituents of the vessel are of synthetic resin, preferably optically transparent, e.g. polystyrene, polyethylene, polylactic acid, polyethylenterephthalate, polycarbonate, or acrylnitril-butadien-styrol, or nylon.

Preferably, the constituents of synthetic resin that are fixed to one another by clamping on their surfaces that are sliding over one another e.g. when mounting constituents, have grooves that are in perpendicular to the common longitudinal axis, e.g. in perpendicular to the longitudinal axis of the shaft. The grooves are e.g. produced by additive manufacturing, preferably by 3D-printing of a liquified resin 3d-printing, for example using high precision fused deposition molding (FDM) technique.

The magnetic shaft drive is drivable by a magnetic drive that has correspondingly arranged magnets, preferably the same number of pairs of magnets as the shaft drive.

Preferably, the first bearing is connected to the lid, preferably inside a recess formed by cylindrical side walls of the lid, e.g. by clamping, and the lid is connected to the first end section of the housing by clamping. This allows the vessel to be provided as separate elements which are simple to connect by clamping without additional fixation means necessary, e.g. without additional glue, sealing or mechanical fastening devices.

The vessel can be provided as a combination of a housing having at its second end section a detection section with at least one, preferably at least two optically transparent windows, the housing containing the stator, and at its first end section having a recess for receiving a lid, and as a separate part a lid connected to the first bearing containing the shaft with the rotor fixed at its second end and the magnetic shaft drive fixed at its first end, the lid being clampable to the first end of the housing.

The reaction vessel has the advantage that it is set up to exert a shear force between the rotor and the stator and, by rotating the rotor, to provide a pumping action onto the liquid that results in a homogenous processing of the entire liquid within the vessel, resulting in presence of liquid that is representative for the entire liquid in the detection section of the housing. The circumferential collar extending over the radius of the cylindrical rotor section upon rotation can generate sufficient centrifugal force to the liquid for exerting a pumping action onto the liquid such that the liquid circulates through the gap between rotor and stator and returns through the channel formed by the spacing between the housing and the stator.

The pumping action is provided only by rotation of the rotor, and accordingly the driven, e.g. rotating, elements of the vessel preferably consist of the rotor arranged on the second end of the shaft and the shaft drive arranged on the first end of the shaft. Further, the vessel has the advantage of exerting significant shear force onto the liquid essentially only between the rotor and the stator, so that the shear force can be controlled by controlling the rotation speed of the rotor only, while the vessel is set up to avoid generating relevant shear forces outside of the defined ring-shaped gap between rotor and stator. Accordingly, the vessel is set up for subjecting liquid to maximal shear force only in the ring-shaped gap between rotor and stator. The vessel is set up for circulating the entire volume of the liquid through the ring-shaped gap between rotor and stator when rotating the rotor, exerting the maximal shear force for converting a native conformation prion protein to its aggregated state only in the ring-shaped gap between rotor and stator, while the flow of liquid through the vessel other than this ring-shaped gap does not provide shear force sufficient to significantly affect the conversion from native conformation prion protein to its aggregated state.

The ring-shaped gap between the rotor and the stator preferably is in the range of 0.2 to 0.5 mm, and/or between 5% and 30% of the radius of the rotor. The shear stress is proportional to the rotation frequency of the rotor, the radius of the rotor, and the viscosity of the liquid, and the shear stress is inversely proportional to the gap width between rotor and stator.

Preferably, at least two vessels are arranged in parallel and are connected to one another, wherein their housings and the connections between them are one piece, e.g. produced as one piece, and further preferably the material of the housings and of the connections between them is continuous. Therein, the at least two vessels that are parallel and connected to one another are arranged such that their optically transparent windows are arranged in common planes, e.g. their windows are arranged in a plane that is parallel to the line of the row along which the vessels are arranged in the arrangement.

Further, the invention provides for an analytical process in which a liquid sample is introduced into the vessel, preferably by introducing a sample into the housing and/or stator and subsequently arranging the rotor inside the stator, preferably by arranging a rotor mounted on a shaft that is run on a first bearing fixed in a lid, while arranging the lid at the first end section of the housing, rotating the magnetic shaft drive for rotating the rotor, optically detecting the sample at the detection section of the housing, and preferably transmitting the detection result or a medical indication derived from the detection result to the originator of the sample. The originator of the sample can be a medical laboratory, a physician or the patient from whom the sample was taken. Further, the analytical process can be used to determine the effect of a compound for its efficacy in retarding or reversing the formation of aggregated conformation prion protein by adding a compound to the sample or to an aliquot of the sample, and comparing the rate of formation of aggregated conformation prion protein during the process. Accordingly, the process can be used for analysing a sample originating from a patient by adding a compound suspected to have activity on the formation of aggregated conformation prion protein to the sample that originates from a specific patient for detecting the efficacy of the compound to at least delay aggregated prion protein formation in the sample of the originator. The efficacy of a compound to delay the formation of aggregated prion protein includes prevention of, retarding, suppressing and/or reversing the formation of aggregated prion protein. Therein, the process can be used to select a compound for its efficacy in delaying, e.g. retarding, supressing, preventing or reversing the formation of aggregated conformation prion protein for a specific patient sample. Generally, a sample can be a liquid or solid biopsy obtained from a patient, e.g. liquor, serum, tissue. The patient can be a human patient or, especially for research, an animal or a tissue culture. The process is an in vitro process or assay, and the process can be used as a translational assay system e.g. during drug discovery.

The process using the device of the invention can also be employed for screening and selecting compounds for their activity and efficacy in retarding, supressing or reversing the formation of aggregated conformation prion protein, the process comprising the step of introducing a liquid sample comprising native prion protein and/or aggregated conformation prion protein, and adding at least one compound to be screened into the housing and arranging the rotor inside the stator, rotating the magnetic shaft drive for rotating the rotor, optically detecting the sample at the detection section of the housing, for detecting a compound having activity for delaying the formation of aggregated prion protein.

Figures 2, 3:
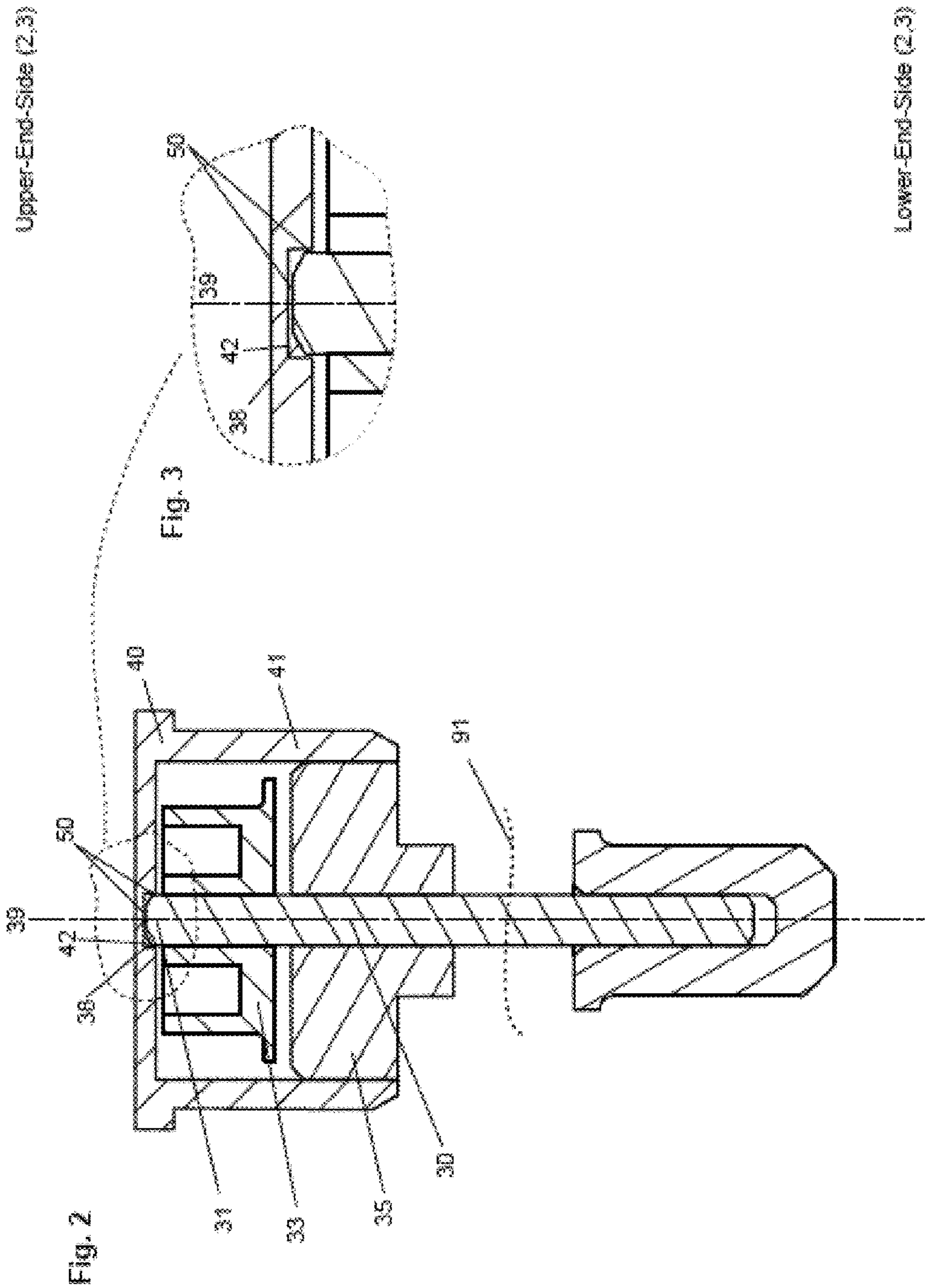

The invention is now described in greater detail by way of an example and with reference to the figures, which show in FIG. 1A a cross-section of an embodiment of the vessel, FIG. 1B a cross-section at the indicated level B and rotated about the horizontal by 90°, FIG. 1C a cross-section at the indicated level C and rotated about the horizontal by 90°, FIG. 1D a cross-section of the housing of FIG. 1A, rotated about the vertical by 90°, where the components of part of an embodiment shown in FIG. 2 have been removed from FIG. 1A.

FIG. 2 a cross-section of part of an embodiment,

FIG. 3 an enlarged section of FIG. 2, and in

Figure 4:
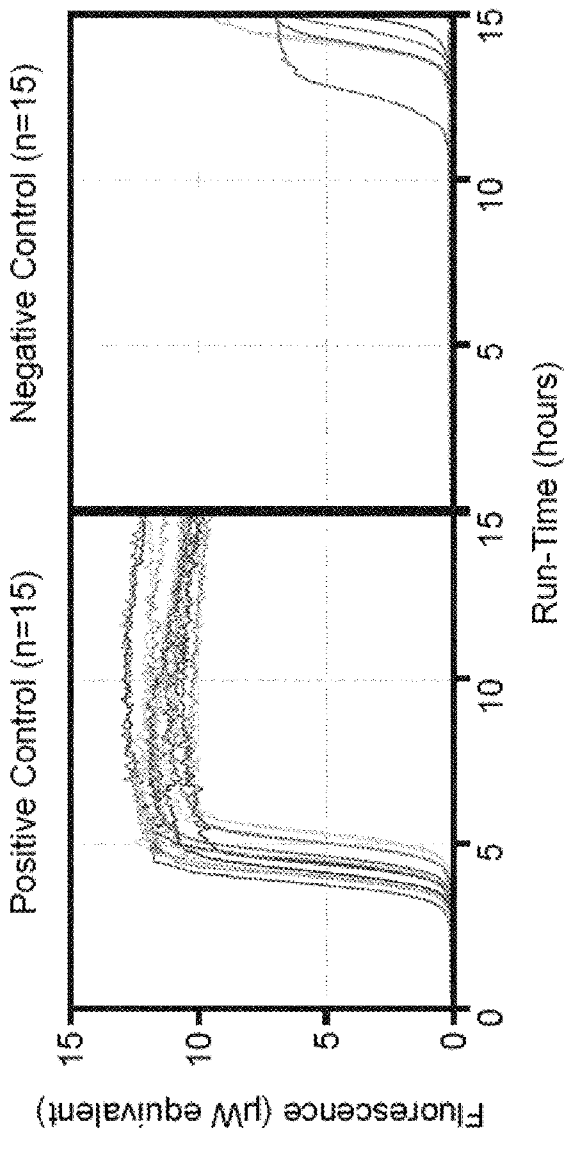

FIG. 4 measurement results of formation of aggregate conformation prion protein generated in a vessel of FIG. 1.

Generally, each feature described with reference to the figures is a separate feature of the vessel of the invention, independent from other features.

FIGS. 1A to D show a housing 1 having a first end section 2 and at its opposite end a second end section 3, which is closed by a bottom wall 4. A detection section 5 is arranged in the second end section 3 of the housing 1, which detection section 5 has at least one, preferably two opposite window sections 6, which are optically transparent (FIG. 1C, FIG. 1D). Optionally, the bottom wall 4 has a bottom window 4*a* of an optically transparent material, with its central section encircled by a non-transparent bottom wall forming a bottom aperture 4*b*.

Inside the housing 1, a stator 10 is arranged, which from its open first end cross-section 11 extends to an opposite open second end cross-section 12, having a cylindrical inner surface 15. At the second end cross-section 12, an extension pipe 13 is connected, which tapers towards the second end section 3 of the housing 1. The extension pipe 13 serves to guide liquid that flows along the extension pipe 13 and the stator 10 through the detection section 5.

Preferably, as shown for the extension pipe 13, the extension pipe 13 tapers towards the second end section 3 of the housing 1, forming a nozzle.

The stator 10 is arranged to the housing with a spacing by webs 14. The stator 10 extends along a stator holding section 8 of the housing 1, and preferably the webs 14 extend between the housing 1 and the stator 10 and along the stator holding section 8.

The rotor 20 is arranged co-axially inside the stator 10, the spacing between rotor 20 and cylindrical inner surface of the stator 11 forming a ring-shaped gap, in which upon rotation of the rotor 20 shear force is applied onto liquid. The rotor as a cylindrical section 21 which is arranged within the stator 10, and the cylindrical section 21 at its first end 22 has a terminal circumferential collar 23 extending over the radius of the cylindrical rotor section 21. The rotor collar 23 in accordance with a preferred embodiment also extends over the ring-shaped gap between the rotor 20 and the stator 10.

The opposite second end 24 of the rotor has a flat front surface 25 with a circumferential bevel 26.

The rotor 20 is arranged on the second end 32 of a shaft 30. Opposite the second end 32, the first end 31 of shaft 30 carries a magnetic shaft drive 33, which includes at least two magnets 34. The magnetic shaft drive 33 is fixed to the shaft 30, which runs in a first bearing 35, wherein the shaft 30 optionally is axially displaceable. In the embodiment shown, the magnetic shaft drive 33 has a flat front surface 36 which can run with friction over an adjacent flat front surface 37 of the first bearing 35, which limits the axial movement of the shaft 30. The first bearing 35 is held by clamping inside a cylindrical section 41 of a lid 40, which cylindrical section 41 is clamped to the first end section 2 of housing 1. The lid 40 also closes the cross section of the first end 2 of the housing 1.

In the embodiment shown, all the elements are arranged co-axially to the longitudinal axis 39 of shaft 30.

As preferred, FIGS. 1A and D show a housing 1 having a collar section 82 between the first end section 2 and the stator holding section 8 of the housing. and from the stator holding section 8, From the first end section 2 the collar section 82 tapers along a first section 82*a* to a reduced cross-section of the housing 1, and from the stator holding section 8, the collar section 82 tapers along a second section 82*b* to the reduced cross-section of the housing 1. The collar section 82 provides for a threshold against movement of liquid from the stator holding section 8 towards the first end section 2 of the housing 1. Preferably, liquid is introduced into the housing at maximum up to the reduced cross-section of the collar section 82, reaching e.g. an approximate liquid filling level 91 at the reduced cross-section of the collar section 82.

The section of the housing 1 in which the extension pipe 13 is arranged, is also referred to as nozzle holding section 83 of the housing. Preferably, the extension pipe 13 is only connected to the stator 10, i.e. without webs extending between the extension pipe 13 and the nozzle holding section 83. Preferably, a first section 83*a* of the nozzle holding section 83 extends for the axial extension of the extension pipe 13 and is spaced from the extension pipe 13 by a constant distance, and the housing 1 adjacent to the first section 83*a* in a second section 83*b* of the nozzle holding section 83 can taper towards the second end section 3 of the housing 1. Therein, the second section 83*b* of the nozzle holding section 83 connects the first section 83*a* to the second end section 3 of the housing 1 across the portion, into which the extension pipe 13 does not extend.

FIG. 2 in an enlarged view shows lid 40, in the cylindrical section 41 of which the first bearing 35 is clamped. The shaft 30 runs in the first bearing 35 and at its first end 31 is attached by clamping to the magnetic shaft drive 33. The first end 31 of the shaft 30 in accordance with a preferred embodiment ends in a convex front surface 38, which runs in a corresponding recess 42 in the lid, the front surface 38 of shaft 30 forming a second bearing 50 with the corresponding recess 42 of lid 40.

FIG. 3 shows an enlarged section of FIG. 2, depicting the second bearing 50.

Generally, the Figures show an embodiment of the vessel according to the invention, in which the vessel is provided as two separate elements, each of which is pre-assembled to be connected to one another to form the hermetically closed reaction vessel by clamping the lid 40 onto the second end section 2 of housing 1, whereby the lid 40 closes the cross section spanned open by the second end section 2 of housing 1, while arranging the rotor 20 co-axially within stator 10.

For the analytical process of the invention, it is preferred to introduce a liquid sample into the housing 1 prior to attaching the lid 40 to the housing.

Example: Analytical Process for Detecting the Influence of Shear Force onto a Sample with Optical Detection As an exemplary sample, a recombinant aggregated prion protein derived from a shear-force induced reaction of recombinant native prion protein with a post-mortem brain homogenate sample originating from a synucleopathy disease patient was mixed at a dilution of 1/100000 with 1.5 mg/ml native conformation human α-synuclein in PBS containing 1% Triton X-100 (positive control). The buffer composition and the procedural details were analogous to the previous disclosures WO 2012/110570 A1 and WO 2016/001334 A1. The Fluorophore used for aggregated prion protein detection was Thioflavin T. As a negative control, the same reaction composition was used without the addition of recombinant aggregated prion protein. The vessel generally corresponded to FIG. 1. The gap width between the stator and the rotor was 0.3 mm and the diameter of the rotor was 3 mm. The utilized processing frequency was 400 revolutions per second (400 Hz) and the reaction temperature was set to 30° C., corresponding to a shear-rate of 12570 per second and to a shear-stress of 11.2 pascal. Overall, the reaction was followed for 15 hours corresponding to 180 cycles of processing and resting. In each cycle, the processing was applied for three seconds, followed by a resting phase of 297 seconds. Fluorescence signals of Thioflavin T were accumulated during the resting phase of each cycle to detect the build-up of aggregated prion protein. For each, positive control and negative control, data-traces for 15 replicas were recorded.

In the positive controls, aggregated conformation prion protein was building up after about 4 hours (±0.5 hours). In the negative control, aggregated conformation prion protein was beginning to build up after about 14 hours in some replicas, while most did not show signs of aggregated conformation prion buildup during the time of observation. The measurement results are shown in FIG. 4, with the positive controls (left) and negative controls (right). As the aggregated conformation buildup occurred in a reproducible manner, individual measurements overlap.

Generally, detection can be measured through the detection section of the vessel by the change of fluorescence of a fluorescent dye added to the mixture, the dye being specific for aggregated conformation prion protein. Exemplary dyes are e.g. Thioflavin T, Thioflavin S, Congo Red, thiophene-based amyloid ligands like luminescent conjugated polythiophenes (LCP), polythiophene acetic acid (PTAA) and luminescent conjugated oligothiophenes (LCO), Pittsburgh compound B, Aminonaphthalene 2-Cyanoacrylate (ANCA) probes, pegylated phenylbenzoxazole derivatives, Pinacyanol, Chrysamine G, and dyes containing at least one of the following scaffolds: Chalcone, Flavone, Aurone, Stilbene, Diphenyl-1,2,4-oxadiazole, Diphenyl-1,3,4-oxadiazole, Benzothiazole, Benzooxazole, Benzofuran, Imidazopyridine, Benzimidazole, Quinoline, Naphthalene.

In the alternative, the native conformation prion protein can be labelled with a fluorescent dye, e.g. by binding of a fluorescent dye to the native conformation prion protein directly or by an intermediate spacer, e.g. fluorophore derivatives that contain reactive chemical groups such as isothiocyanates (reactive to primary amines, e.g. Lysines), succinylimide esters (reactive towards amino groups to form amido bonds, e.g. N-terminal amino acids), maleimide (reactive to free sulfhydryl groups, e.g. cysteine). Such fluorophore derivatives include cyanines, flurescein, rhodamine, Alexa Fluors, Dylight fluors, ATTO-Tec Dyes, BODIPY Dyes, SETA Dyes, SeTau Dyes, DYOMICS Dyes.

| Reference numerals: | |
|---|---|
| 1 | housing |
| 2 | first end section of housing |
| 3 | second end section of housing |
| 4 | bottom wall |
| 4a | bottom window |
| 4b | bottom aperture |
| 5 | detection section |
| 6 | window section |
| 7 | cylindrical section |
| 8 | stator holding section of the housing |
| 10 | stator |
| 11 | first end cross-section of stator |
| 12 | second end cross-section of stator |
| 13 | extension pipe |
| 14 | web |
| 15 | cylindrical inner surface of stator |
| 16 | opening |
| 20 | rotor |
| 21 | cylindrical section of rotor |
| 22 | first end of rotor |
| 23 | collar of rotor |
| 24 | second end of rotor |
| 25 | front surface of rotor |
| 26 | bevel |
| 30 | shaft |
| 31 | first end of shaft |
| 32 | second end of shaft |
| 33 | magnetic shaft drive |
| 34 | magnet |
| 35 | first bearing |
| 36 | front surface of magnetic shaft drive |
| 37 | front surface of first bearing |
| 38 | front surface of shaft |
| 39 | longitudinal axis |
| 40 | lid |
| 41 | cylindrical section of lid |
| 42 | recess in lid |
| 50 | second bearing |
| 82 | collar section of the housing |
| 82a | first section of the collar section |
| 82b | second section of the collar section |
| 83 | nozzle holding section of the housing |
| 83a | first end of the nozzle holding section |
| 83b | second end of the nozzle holding section |
| 91 | approximate liquid filling level |

The invention claimed is:

1. A vessel for use in the analysis of samples, comprising:

a lid;

a housing having a first end section for connecting to the lid and a second end section opposite the first end section, wherein the second end section is closed by a bottom wall, wherein the second end section comprises a detection section which comprises a housing wall that has at least one optically transparent window section, wherein the lid closes the first end section of the housing;

a rotor with a cylindrical section;

a stator arranged inside the housing, wherein the stator comprises a cylindrical inner surface for receiving the rotor with a constant spacing, wherein the cylindrical inner surface has an open first end cross-section and a second end cross-section opposite the first end cross-section, wherein an outer surface of the stator is arranged with a spacing from the housing;

at least two webs connecting the stator to the housing with the spacing;

a magnetic shaft drive; and a shaft comprising a first end to which the magnetic shaft drive is fixed and a second end opposite the first end, wherein the second end of the shaft is covered by the rotor, wherein the cylindrical section of the rotor is arranged within the stator, wherein the rotor and the stator are spaced by a ring-shaped gap of constant radius, wherein the rotor has a second end (24) that covers the second end of the shaft, wherein the rotor has at the first end of the rotor a terminal circumferential collar extending over a radius of a cylindrical rotor section and extending over a cylindrical surface of the stator (10), wherein the shaft is run in a first bearing that is arranged on the shaft in an axial section arranged between the magnetic shaft drive and the rotor, the first bearing is fixed to the lid, and wherein the shaft, the magnetic shaft drive, the first bearing, the rotor, the stator and/or the detection section are arranged co-axially.

2. The vessel according to claim 1, wherein the stator, the housing, and the at least two webs spacing the stator from the housing are formed as one piece.

3. The vessel according to claim 1 wherein the at least one optically transparent window section of the detection section comprises two window sections in opposite wall sections of the housing wall, wherein the two window sections are optically transparent in alignment.

4. The vessel according to claim 1 wherein the detection section is arranged adjacent to the bottom wall of the housing.

5. The vessel according to claim 1 wherein the lid has a cylindrical section of side walls forming a recess arranged coaxially to the housing, wherein the cylindrical section of side walls is configured for clamping to a cylindrical section of the first end section of the housing.

6. The vessel according to claim 1 wherein the second end cross-sectional opening of the stator is directly adjacent to the detection section or is spaced from the detection section.

7. The vessel according to claim 1 further comprising an extension pipe connected to the stator at the second end cross-section, wherein the extension pipe terminates directly adjacent to the detection section or at a spacing from the detection section.

8. The vessel according to claim 7, wherein the extension pipe has a cross-section tapering towards the detection section or has a constant cross-section.

9. The vessel according to claim 1 wherein the second end of the rotor has either a flat front face and a bevelled or rounded circumferential edge, or a rounded front face.

10. The vessel according to claim 1 wherein the terminal circumferential collar extends over a ring-shaped gap formed between the rotor and the stator.

11. The vessel according to claim 1 wherein the first end of the shaft is a free end that is arranged in a recess of the lid, wherein the first end of the shaft and the recess of the lid form a second bearing, which is a frictional bearing.

12. The vessel according to claim 1 wherein the housing, the stator arranged inside the housing, and the detection section are configured as a first element, and wherein a second element is configured from the lid connected to the first bearing in which the shaft is run, wherein the first end of the shaft is attached to the magnetic shaft drive and wherein the magnetic shaft drive is arranged between the first bearing and the lid, and wherein the first end of the shaft is a free end and is arranged in a recess of the lid, and wherein the first end of the shaft and the recess of the lid form a second bearing with the rotor attached to the second end of the shaft.

13. The vessel according to claim 12, wherein the first end section of the housing has a cylindrical section that is adapted to receive the lid with a clamping fit.

14. A process for analyzing a sample originating from a patient for detecting a presence of aggregated prion protein using a vessel according to claim 1, comprising:

introducing the sample and native prion protein into the housing, arranging the rotor inside the stator, rotating the magnetic shaft drive for rotating the rotor, optically detecting the sample at the detection section of the housing, and transmitting the detection result or a medical indication derived from the detection result to an originator of the sample.

15. The process according to claim 14, further comprising adding a compound to the sample originating from the patient for detecting the efficacy of the compound to at least delay aggregated prion protein formation in the sample of the originator.

16. A process for screening compounds for activity in suppressing formation of aggregated prion protein, using a vessel according to claim 1, comprising:

introducing a liquid sample comprising native prion protein and/or aggregated conformation prion protein into the vessel;

adding at least one compound to be screened into the housing;

arranging the rotor inside the stator, rotating the magnetic shaft drive for rotating the rotor, optically detecting the sample at the detection section of the housing, and identifying a compound having activity for delaying the formation of aggregated prion protein.

* * * * *